United States Patent [19]
Kunioka et al.

[11] 3,954,119
[45] May 4, 1976

[54] SYSTEM FOR MEASURING AND CONTROLLING THE CONCENTRATION OF AN EMULSION

[75] Inventors: Kazuo Kunioka; Shuzo Fukuda, both of Yokohama; Kinya Inamoto, Kawasaki, all of Japan

[73] Assignee: Nippon Kokan Kabushiki Kaisha, Tokyo, Japan

[22] Filed: June 13, 1974

[21] Appl. No.: 479,113

[30] Foreign Application Priority Data

| June 22, 1973 | Japan | 48-70570 |
| July 19, 1973 | Japan | 48-80460 |
| Apr. 30, 1974 | Japan | 49-48587 |
| Apr. 30, 1974 | Japan | 49-48588 |

[52] U.S. Cl. .................................... 137/92; 72/236
[51] Int. Cl.² ........................................ B21B 27/06
[58] Field of Search ............. 137/88, 92; 73/61.1 R, 73/53

[56] References Cited
UNITED STATES PATENTS

| 3,275,018 | 9/1966 | Roberts | 137/92 X |
| 3,480,032 | 11/1969 | Collins, Jr. | 137/92 |
| 3,770,020 | 11/1973 | Tamura et al. | 73/53 X |
| 3,791,200 | 2/1974 | Hayle | 73/61. R X |
| 3,859,846 | 1/1975 | Asada et al. | 73/61.1 R X |

*Primary Examiner*—William R. Cline
*Attorney, Agent, or Firm*—Flynn & Frishauf

[57] ABSTRACT

A system for measuring and controlling the concentration of an emulsion, wherein a measuring pipe included in an emulsion feed line is fitted with an emulsion concentration-detecting device; the ultrasonic wave transmitter of the concentration-detecting device sends forth ultrasonic waves into an emulsion running through a circulation line so as to be caught by an ultrasonic wave receiver; the concentration-detecting device generates an output signal corresponding to the velocity with which ultrasonic waves are propagated from the ultrasonic wave transmitter to the ultrasonic wave receiver, utilizing the fact that the velocity of said propagation is substantially proportional to the concentration of an emulsion flowing through the circulation line, and also delivers an output signal corresponding to temperature variation from a detection terminal through a transducer to a circuit for correcting the measured concentration of the emulsion according to temperature variation in view of the fact that the propagation velocity of the emulsion varies with temperature; and said concentration-correcting circuit generates a control signal exactly corresponding to the actual concentration of the emulsion by correcting an output signal from the concentration-detecting device which denotes the measured propagation velocity of ultrasonic waves, thereby controlling the concentration of the emulsion to maintain a prescribed level throughout the circulation line.

17 Claims, 14 Drawing Figures

SYSTEM FOR MEASURING AND CONTROLLING THE CONCENTRATION OF AN EMULSION

This invention relates to a system for measuring and controlling the concentration of an emulsion which is capable of automatically and continuously measuring the concentration of an emulsion and also properly controlling said concentration from the results of measurement, and more particularly to a system for measuring and controlling the concentration of an emulsion prepared from a mixture of oil and water to be used as a lubricant, for example, in a cold rolling mill.

An emulsion used for lubrication of a rolling mill consists of palm oil or animal or vegetable oil having a good lubricating capacity mixed with water. This emulsion is generally referred to as "a rolling oil". Since oil is insoluble in water, the "rolling oil" is prepared by adding an emulsifying agent to the mixture of oil and water or by forceful emulsification of said mixture through application of mechanical agitation.

Where an emulsion, or more specifically, "the rolling oil" consisting of two essentially insoluble components is allowed to stand for some minutes, the two components readily segregate from each other. The separated oil floats up, with the result that the amount of oil still remaining in an emulsified state decreases, exerting a harmful effect on the shape, surface finish and condition of rolled product and the rolling speed when said emulsion is used as the so-called "rolling oil" for a rolling mill. Therefore, it is very important for rolling operation periodically to measure and control the concentration of an emulsion so as to enable it to run through a circulation line at a prescribed concentration.

Further, the emulsion is generally subject to age hardening during circulation. Also from this point of view, the concentration of the emulsion should be periodically measured and controlled.

One of the known methods of measuring the concentration of an emulsion (or "rolling oil") consists in sampling a prescribed amount of emulsion and chemically analyzing the sample.

The prior art measuring method runs as follows. About 10cc of concentrated sulfuric acid and concentrated pitric acid respectively are added to a sample of emulsion having a volume of about 100cc, followed by application of heat to about 70°C. Then the oily component kept in an emulsified state up to this point segregates from water and floats up. The oily component collected in the upper part of the sample is taken out to measure its volume, thereby determining the concentration of said oil.

Though practicable with relative ease, the conventional batch process of measurement has the drawbacks that even a skilled operator takes a longer time than 15 minutes to finish measurement and moreover is likely to commit gross errors in determining the volume of the separated oily component. Further, this customary process fails to measure the concentration of an emulsion directly while it is running through a circulation line and carry out said measurement continuously.

Another customary method of measuring the concentration of a liquid flowing through a circulation line is to determine the concentration of said liquid from its density. This method is practically applied by fitting a pipe line for manufacture of petroleum product with an instrument operated by the principle of measuring the density of a liquid conducted through said pipe line. Other known processes for measuring the concentration of a liquid are carried out, for example, by determining the mechanical resonance characteristics, dielectric constant and radiation penetrability of a liquid. These process, too, indeed attain the continuous measurement of the concentration of a liquid, if an instrument is provided on a pipe line.

However, any of the above-mentioned processes is not adapted to measure the concentration of an emulsion used for lubrication of a rolling mill. The reason is that an emulsion used in this particular field contains considerable amounts of fine particles of dirt and minute grains of iron, and the presence of such foreign matter mainly gives rise to noticeable errors of measurement. Required elimination of dirt and iron grains by means of a filter has rendered accurate determination of the concentration of a rolling mill emulsion extremely complicated and time-consuming. Since dirt and iron grains are difficult of complete removal even by means of a filter, the above-mentioned various continuous processes used in measuring the concentration of a liquid running though the pipe line of the petroleum product industry are unadapted to determine the concentration of a lubricant emulsion used in a rolling mill.

The above-mentioned chemical sampling method of measuring the concentration of an emulsion which is practically adopted in a rolling mill is manually to control the concentration of an emulsion running through a circulation line by an operator at an optional time interval at his discretion, namely, by the so-called batch process. Such batch process, however, presents difficulties in maintaining the desired concentration of an emulsion and fails to attain the stable operation of a rolling mill and provide high quality rolled product. Moreover, this batch process requires a great deal of manpower and time, resulting in the high cost of product and the decreased rolling efficiency. In view of the above-mentioned circumstances, strong demand has been made for a system capable of periodically and automatically measuring the concentration of an emulsion while it is allowed to run continuously and effecting the automatic control of said concentration in order to maintain said concentration at a desired level.

This invention relates to a system for measuring and controlling the concentration of an emulsion by the fundamental principle of emitting ultrasonic waves into an emulsion running through a measuring pipe to detect the velocity with which the ultrasonic waves propagate through the emulsion and determining the concentration from the velocity of propagation. As used herein, the term "ultrasonic waves" means those having a frequency of 1 mega herts units. To this end, the system of the invention for measuring and controlling the concentration of an emulsion comprises a device for detecting the velocity with which ultransoic waves propagate through an emulsion. Said detecting device comprises an ultrasonic wave transmitter for sending forth ultrasonic waves through an emulsion flowing through a measuring pipe and an ultrasonic wave receiver, both being fitted to the measuring pipe. The detecting device also includes a correction circuit for correcting the measured propagation velocity of ultrasonic waves by the extent of temperature variation in view of the fact that the velocity with which ultrasonic waves propagate through an emulsion varies with temperature. Detection by the detecting device of this invention has the advantage of being substantially free from the effect of impurities, for example, dirt and iron grains contained in an emulsion and always indicating the actual concentration of an emulsion. Moreover, errors of measurement caused by temperature variation are automatically corrected within said detecting device itself, thereby enabling an output signal denoting the actual concentration of an emulsion to be generated by said detecting device.

The above-mentioned ultrasonic wave transmitter and receiver included in the detecting device need not be fitted to the wall of the measuring pipe. For example, according to an embodiment of this invention, the ultrasonic wave transmitter and receiver are supported on a rectangular frame. This frame is provided with a plate for reflecting ultrasonic waves emitted, thereby fixing the length of the course through which ultrasonic waves propagate through an emulsion from the transmitter and receiver. This support frame is placed in an emulsion running through a measuring pipe when the concentration of an emulsion therein is to be measured. Where it is desired to measure said concentration in an emulsion tank, it is advised to place said support frame therein.

The emulsion concentration-measuring system of this invention further includes a control device which is supplied with a control output signal from the detecting device which corresponds to the measured concentration of an emulsion flowing through a circulation line and automatically corrects said measured concentration by said control output signal. Since the control device controls the concentration of an emulsion running through the circulation line periodically and automatically while the emulsion is allowed to run continuously, said concentration is maintained at a proper level, attaining the quality improvement of rolled product and the higher rolling efficiency.

With an emulsion concentration-measuring system according to a second embodiment of this invention, there is provided an exclusive measuring pipe line which is connected to an emulsion tank unlike the measuring pipe of the preceding embodiment which is disposed in the circulation line of an emulsion. The exclusive measuring pipe line of the second embodiment is provided inside with not only a detecting device but also a foam-removing device including a filter so as to attain the more accurate measurement of the concentration of an emulsion. Since an emulsion divorted into the exclusive measuring pipe line flows slowly, an oily component segregated from the emulsion is likely to stick to the inner wall of the measuring pipe. To avoid such occurrence, a vortical stream-generating device is provided in that part of the pipe line where the detecting device determines the concentration of an emulsion. The installation of said vortical stream-generating device prevents the segregated oily component from being attached to the inner wall of the measuring pipe located at the detection point, thus eliminating that harmful effect on the reflection of sound waves which might otherwise arise from the deposition of the segregated oily component on the inner wall of the measuring pipe, and in consequence attaining the more accurate detection of the propagation velocity of ultransoic waves.

Accordingly, the primary object of this invention is to provide a system for measuring and controlling the concentration of an emulsion which is capable of effecting said measurement automatically and periodically while the emulsion is allowed to run continuously and automatically controlling said concentration from the results of measurement so as to maintain said concentration at a prescribed level.

A second object of the invention is to provide a system for measuring and controlling the concentration of an emulsion, which is particularly adapted to measure and control the concentration of an emulsion used for lubrication of a rolling mill.

A third object of the invention is to provide a system for measuring and controlling the concentration of an emulsion which is capable of elevating the operating efficiency of machinery using an emulsion and maintaining the high quality of mechanically treated product.

A fourth object of the invention is to provide a system for measuring and controlling the concentration of an emulsion, which is provided with a device for removing air bubbles carried through a circulation pipe line along with an emulsion.

A fifth object of the invention is to provide a system for measuring and controlling the concentration of an emulsion, which is provided with a device for generating a vortical stream in an emulsion in that part of a circulation pipe line where the concentration of the emulsion is to be detected, thereby preventing an oily component segregated from the emulsion from sticking to the inner wall of the pipe located at said detecting point.

Futher objects and advantages of the invention can be more fully understood from the following detailed description taken in conjunction with the accompanying drawings.

Figure 1:
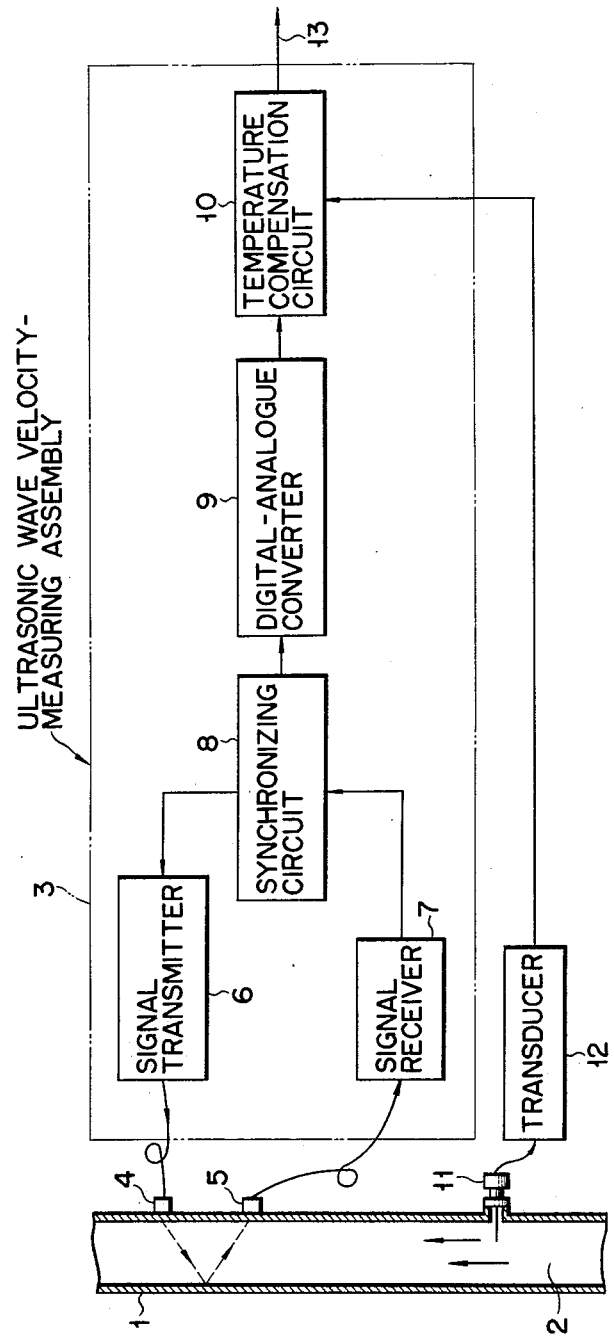
FIG. 1 is a block circuit diagram of a detecting device included in a system according to an embodiment of this invention for measuring and controlling the concentration of an emulsion.

Referring to FIG. 1, the measuring pipe 1 of an emulsion concentration-detecting device constitutes part of a circulation line of a lubricant emulsion used as the so-called rolling oil.

According to the first embodiment of this invention, to the measuring pipe 1 consists of a carbon steel pipe 6.0 mm thick and 216.3 mm in outer diameter. However, this measuring pipe 1 may be separately provided in the form of an exclusive measuring pipe line 66 as used in the later described another embodiment of the invention. A fluid or emulsion 2 being measured runs through the measuring pipe 1. In this case, the velocity with which ultrasonic waves propagate through the emulsion 2 is measured by an ultrasonic wave velocity-measuring assembly 3 included in a block indicated in broken lines (FIG. 1) as a basic factor in determining the proportion of the oily component of the emulsion 2 or its concentration.

The ultrasonic wave transmitter 4 and receiver 5 are fixed to the outer wall of the measuring pipe 1 by suitable adhesive, for example, epoxy resin adhesive (manufactured by Ciba Ltd. under a commercial name "Araldite"). For firmer bonding of said transmitter and receiver 4, 5 it is advised to fix them in place by a proper belt. The ultrasonic wave transmitter 4 consists of a known electro-acoustic converter formed of, for example, lead zirconate or quartz. An ultrasonic wave receiver 5 consists of a known electro-acoustic converter prepared from, for example, lead zirconate or quartz like the ultrasonic wave transmitter 4, and is fitted to the measuring pipe 1 at a prescribed interval therefrom. Upon receipt of ultrasonic waves from the transmitter 4, the ultrasonic wave receiver 5 sends forth an electric signal. The signal transmitter 6 of the ultrasonic wave velocity-measuring assembly 3 is a pulse generator designed to supply the ultrasonic wave transmitter 4 with an electric signal for giving forth ultrasonic waves. The signal receiver 7 of the ultrasonic wave velocity-measuring assembly 3 amplifies the electric signal delivered from the ultrasonic wave receiver 5. The synchronizing circuit 8 of said assembly 3 is electrically connected to the signal transmitter 6 and signal receiver 7, and, upon receipt of an electric signal from the signal receiver 7, delivers an electric command pulse signal to the signal transmitter 6 and generates an electric output signal corresponding to the propagation velocity of ultrasonic waves. A digital-analogue converter (D-A converter) 9 consists of an integration circuit and is connected to the synchronizing circuit 8 to convert an output delivered therefrom in the form of a frequency signal into a voltage signal. The D-A converter 9 is provided with a temperature compensation circuit 10 of the later described arrangement, which in turn is connected through a transducer 12 to a temperature detecting section 11 fitted to the measuring pipe 1. This temperature detecting section 11 supplies the temperature compensation circuit 10 with an electric signal corresponding to the temperature of an emulsion 2. The temperature compensation circuit 10 corrects errors in the measured propagation velocity of the emulsion 2 which are caused by temperature variation and generates a final output signal 13 exactly corresponding to the actual concentration of the emulsion 2 and denoting a value of voltage. Said output signal 13 is delivered to the later described control device for regulating the concentration of the emulsion 2.

The ultrasonic transmitter 6, ultrasonic receiver 7, synchronizing circuit 8 and D-A converter 9 constituting the ultrasonic wave velocity-measuring assembly 3 are all of the known type and indicated in blocks. The aforesaid temperature detecting section 11 comprises, for example, a platinum resistance thermometer bulb. The transducer 12 amplifies minute variations in resistance and voltage resulting from temperature changes determined by the temperature detecting section 11 and delivers a signal denoting the amplified voltage to the temperature compensation circuit 10.

An emulsion whose concentration can be determined by the above-mentioned detecting device is not limited to the type which is used for lubrication of a rolling mill. As used herein, the term "emulsion" broadly means a general mixed liquid consisting of a plurality of components. Accordingly, the so-called suspension is also included in the emulsion of this invention.

There will now be described the operation of measuring the concentration of an emulsion using a concentration-detecting device (in the later described embodiment denoted by a referential numeral 41).

Figure 2:
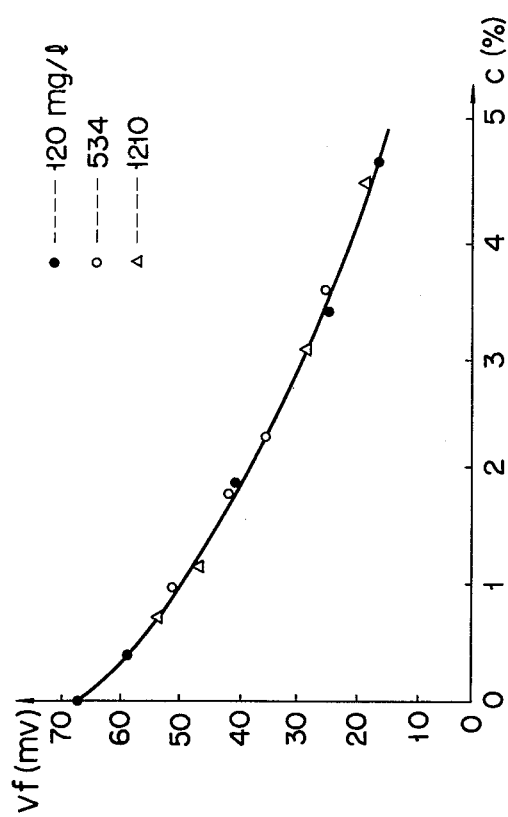
FIG. 2 is a chart showing variations with temperature in the velocity with which ultrasonic waves propagate through the water (shown in a broken line) and the oil (shown in a solid line) alone which are mixed to form an emulsion.

Reference is first made to the chart of FIG. 2 showing the measured relationship between the various temperatures $t$ of the oil and water which are mixed into an emulsion and the velocities $v$ with which ultrasonic waves propagate through the respective components at said temperatures.

The water is city water and the oil is beef tallow. The chart of FIG. 2 shows that ultrasonic waves propagate through the oil (as shown in a solid line) at a much slower rate than through the water (as shown in a broken line) at the same temperature, and the propagation velocity of ultrasonic waves presents wave prominent variations with temperature in the oil than in the water.

Figure 3:
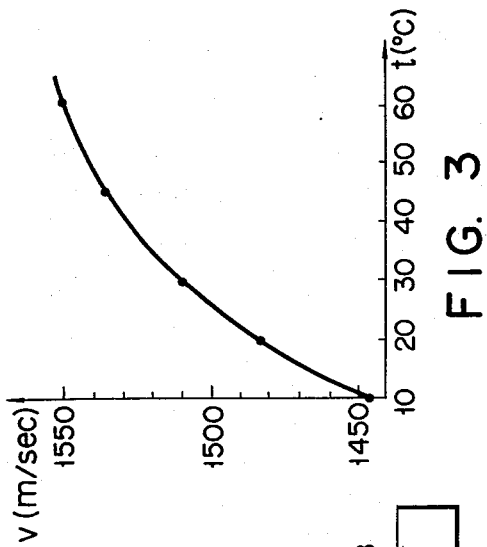
FIG. 3 is a chart indicating variations with temperature in the velocity with which ultransoic waves are transmitted through the emulsion.

The chart of FIG. 3 indicates the results of the present inventors' experiments on the relationship between the various temperatures $t$ of a lubricant emulsion used as the so-called rolling oil in cold rolling and the velocities $v$ of ultrasonic waves propagating through said emulsion at said temperatures. The chart shows that the propagation velocity $v$ of ultransonic waves changes from about 1535 m/sec. to about 1550 m/sec. for the temperatures $t$ of an emulsion ranging from 45° to 60°C.

Reverting to FIG. 1, ultrasonic waves delivered from the transmitter 4 first strike against the inner wall of the measuring pipe 1 and then are reflected therefrom to the ultrasonic receiver 5 as indicated by broken lines bearing arrow marks. The ultrasonic receiver 5 conducts a minute received signal to the signal receiver 7 which in turn amplifies said minute signal and delivers it to the synchronizing circuit 8. Upon receipt of said amplified signal, the synchronizing circuit 8 immediately sends forth a command signal to an ultrasonic transmitter 4, which in turn supplies an output signal to the signal transmitter 6, causing ultrasonic waves to be again sent forth into the emulsion from the ultrasonic transmitter 4.

As mentioned above, ultrasonic waves travel from the transmitter 4 to the receiver 5 and an electric signal generated by said receiver 5 is repeatedly transmitted through a route consisting of the signal receiver 7, synchronizing circuit 8, signal transmitter 6 and ultransonic transmitter 4. Time required per cycle of transmission, namely, the period t0 of said transmission may be expresses as follows:

$$t0 = \frac{l}{v} + \tau$$

where:
$v$ = velocity of ultrasonic waves propagating through a medium
$\tau$ = delay of time due to an electric signal being transmitted through the above-mentioned circuit
$l$ = a length of course covered by ultrasonic waves while they travel from the transmitter 4 to the receiver 5

Therefore, the frequency of a signal corresponding to the propagation velocity of ultrasonic waves which is transmitted from the synchronizing circuit 8 to the D-A converter 9 may be given as follows:

$$f = \frac{1}{t0} = \frac{v}{l+\tau v}$$

In this case, the propagation velocity $v$ of ultrasonic waves varies with the concentration of a medium or the emulsion 2. Since the frequency of the above-mentioned signal from the synchronizing circuit 8 varies with the propagation velocity $v$, it is possible to determine the concentration of the emulsion 2 from said varying frequency. The frequency $f$ of an output signal from the synchronizing circuit 8 is converted into a value of voltage by the D-A converter 9 and conducted to the temperature compensation circuit 10, which is also supplied with a signal corresponding to the temperature of the emulsion 2 delivered from the transducer 12 in the form denoting a value of voltage. Therefore, this value of voltage corrects a value converted from the aforesaid frequency $f$.

Referring to the chart of FIG. 3, where the propagation velocity of ultrasonic waves varying with the temperatures of the emulsion 2 ranging from 45° to 60°C is expressed as changes in the concentration of the emulsion 2, then said changes account for 0 to 5% in the case of the first embodiment. Since the proper concentration of an emulsion practically used with a rolling mill is chosen to be around 5%, the above-mentioned variation of the emulsion concentration caused by temperature change exerts a considerably large effect, thus making it indispensable to carry out temperature compensation in measuring the emulsion concentration.

The temperature compensation circuit 10 of the first embodiment comprises an arithmetic operation unit carrying out the following operation:

$$Vc = aVt + bVf + cVt^2 + dVt \cdot Vf \qquad (1)$$

where:
$Vc$ = a value of voltage corresponding to the emulsion concentration obtained by the operation of the above equation (1)
$Vf$ = a value of voltage corresponding to frequency f
$Vt$ = a value of voltage corresponding to temperature
$a, b, c, d$ = constants defined, for example, by the kinds of oil and circuit arrangement, the values of these constants being determinable by a statistic mathematical process such as regression analysis Strictly speaking, $Vc$ may be indicated by a formula of linear combination consisting of nine terms: $Vt^2 \cdot Vf^2$, $Vt^2 \cdot Vf$, $Vt \cdot Vf^2$, $Vt^2$, $Vf^2$, $Vt \cdot Vf$, $Vt$, $Vf$ and constant. Though usable with this invention, an arithmetic operation unit carrying out such a precise operation is too expensive for practical application. Though $Vc$ may be indicated by a formula of linear approximation, said formula is reduced in the precision of measurement despite the simple circuit arrangement and lower cost, and consequently is unadapted for use with the measuring system of this invention. Further, a circuit for carrying out the operation of the above equation (1) may be formed of an analogue circuit consisting of a combination of a square circuit, multiplication circuit and addition-subtraction circuit. The concrete formation of said analogue circuit is already known to those skilled in the art.

Figure 4:
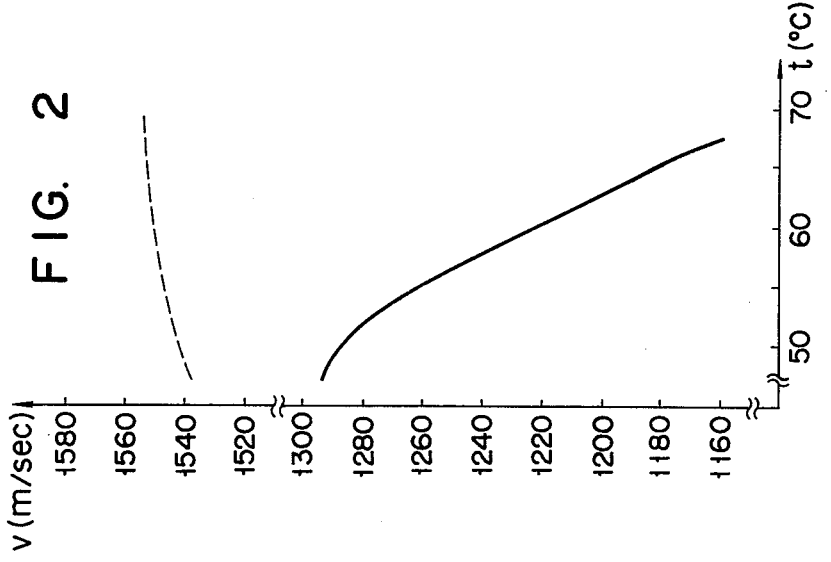
FIG. 4 is a chart proving that the propagation velocity of ultrasonic waves which proportionally varies with the concentration of an emulsion can be accurately determined by the measuring system of this invention substantially without being affected by the amount of impurities contained in the emulsion.

Results of experiments carried out by the above-mentioned emulsion concentration-detecting device of the first embodiment are presented in the chart of FIG. 4. Throughout these experiments, measurement was made in one pipe of a circulation line through which an emulsion for lubrication of a rolling mill was made to flow. The experiments were made by varying the concentration of an emulsion or rolling oil and the amount of fine iron powders contained therein as impurities. Iron powders ranging from 50 to 150 microns in particle size were used in three amounts: 120, 534 and 1210 mg/l indicated in FIG. 4 by a black point ●, a white circle o and a triangular point respectively. Throughout the experiments, the temperature of an emulsion was maintained at 50° ± 0.3°C. The concentration c of the emulsion was plotted on the abscissa of FIG. 4 and the output $V_f$ from the D-A converter was plotted on the ordinate. The concentration of the emulsion was determined by chemical analysis. FIG. 4 shows that the output $V_f$ and the concentration c have a matching relationship expressed by an equation including a square term, and that said matching relationship is little affected by the content of iron powders as impurities. Accordingly, the measurement of the concentration of an emulsion by the detecting device of this invention eliminates the necessity of providing a filter in a pipe disposed near the point of detection for removal of impurities such as iron powders.

According to the foregoing embodiment, the ultrasonic transmitter and receiver 4, 5 were fitted to the same side of the outer wall of the measuring pipe 1. Thus, ultrasonic waves delivered from the transmitter 4 first struck against the inner wall of the measuring pipe 1 and then was reflected therefrom to the receiver 5. However, it is possible to dispose the transmitter and receiver 4, 5 on the mutually facing points on the outer wall of the measuring pipe 1, causing ultrasonic waves to travel linearly from the transmitter 4 to the receiver 5 without reflection.

In addition to the above-mentioned arrangement, the ultrasonic transmitter and receiver 4, 5 may be immersed in an emulsion running through the measuring pipe 1 by being supported on a rectangular frame 14 used in another embodiment of this invention.

Figure 5:
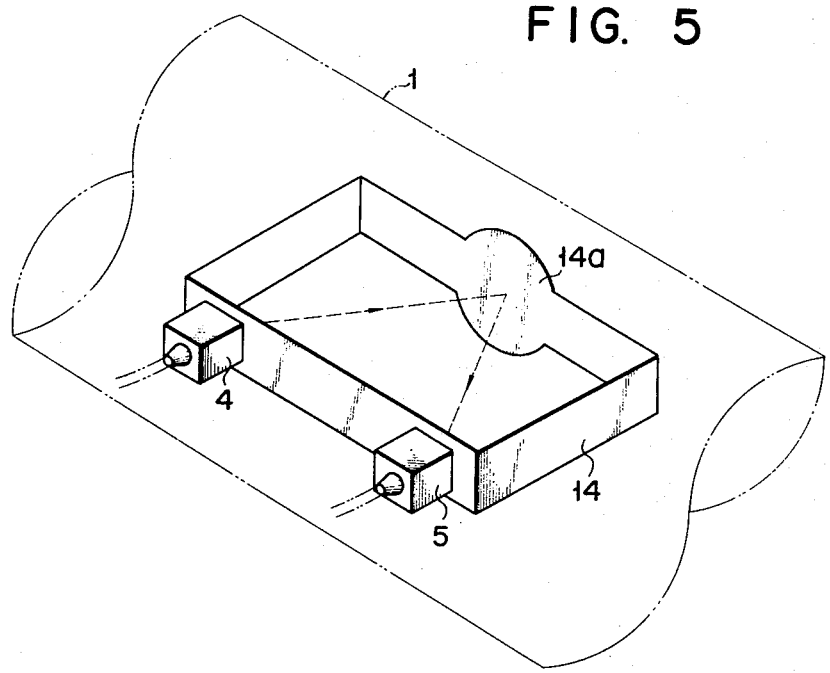
FIG. 5 is a fractional enlarged oblique view of a modification of the detecting device of FIG. 1 according to another embodiment of the invention.

As illustrated in FIG. 5, the rectangular frame 14 is placed in the measuring pipe 1 indicated in chain lines. The ultrasonic transmitter and receiver 4, 5 are fitted in a fully waterproof state at a prescribed interval on one of the parallel lengthwise boards of the frame 14. The opposite lengthwise board has its center fitted with an ultrasonic wave reflector 14a. Ultrasonic waves sent forth from the transmitter 4 travel through the emulsion, strike against the reflector 14a and are reflected therefrom to the receiver 5 by following the course indicated by broken lines bearing arrow marks. The traveling course of the ultrasonic waves has a fixed length due to said waves always following the arrow-indicated direction, thereby attaining the accurate determination of the propagation velocity of ultrasonic waves varying with the concentration of the emulsion. Application of said support frame 14 designed to fix the length of the traveling course of ultrasonic waves can attain the determination of the concentration of the emulsion with the ultrasonic transmitter and receiver 4, 5 placed in the measuring pipe 1. Said support frame 14 can be disposed not only in the measuring pipe 1 but also in an emulsion tank, thus attaining the determination of the concentration of the emulsion in said tank, too.

With the detecting device of this invention, a signal corresponding to the velocity of ultrasonic waves propagating through the emulsion is generated in the form denoting frequency. However, this invention also includes another process of determining the propagation velocity of ultrasonic waves from the time required for said waves to travel through the emulsion from the transmitter 4 to the receiver 5, this process being easily designable by those skilled in the art.

Figure 6:
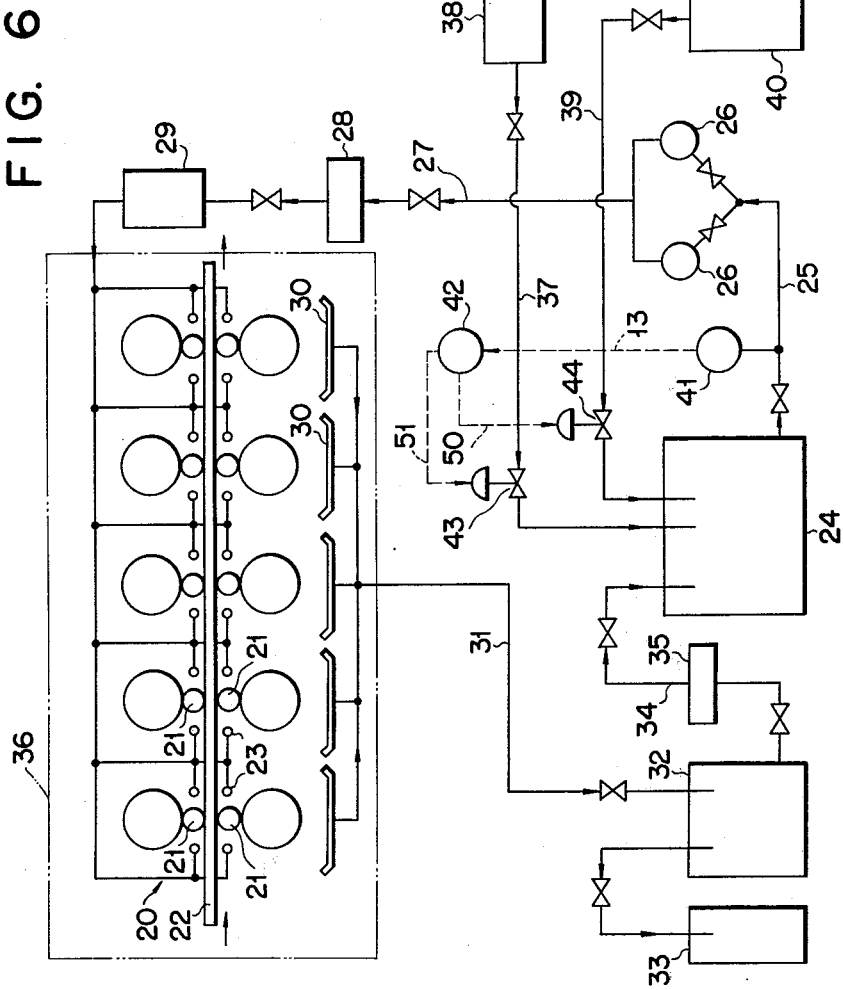
FIG. 6 is a diagram of the entire arrangement of the emulsion circulation line of a rolling mill and a system according to an embodiment of the invention fitted to said circulation line to measure and control the concentration of the emulsion.

FIG. 6 presents the entire arrangement of the emulsion circulation line of a rolling mill and a system according to an embodiment of this invention fitted to said circulation line to measure said concentration and control it to a proper value.

There will now be first briefly described a rolling mill and the circulation line of an emulsion which are of well known arrangement.

A rolling mill 20 supplied with a lubricant emulsion is a 5 stand tandem cold rolling type. A steel strip 22 being rolled is conducted while being rolled in the direction of the arrow of FIG. 6 between two rows of rolls 21 arranged in the upper and lower parts of the rolling mill 20. An emulsion is ejected from a plurality of nozzles 23 into a space between the steel strip 22 and the upper and lower rows of rolls 21. The nozzles 23 are disposed above and below the steel strip 22 between the horizontally adjacent rolls 21. Each nozzle 23 is supplied with an emulsion delivered from an emulsion tank 24 through the later described circulation line.

The emulsion in the emulsion tank 24 is delivered to each nozzle 23 through a feed pipe 25, pump 26, feed pipe 27, filter 28 and cooler 29 in the order mentioned. After used, the emulsion ejected from the nozzles 23 falls into shallow receptacles 30 disposed right below the rolls 21 constituting the lower row. The emulsion collected in the receptacles 30 is generally contaminated with impurities such as dirt and fine iron powders brought in during the rolling operation. The receptacles 30 are provided at the bottom with the discharge ducts which are collectively connected to a connection pipe 31 fitted to a dirt tank 32. Thus, the soiled emulsion is collected by gravity flow in said tank 32 through the discharge ducts and connection pipe 31. In the dirt tank 32, impurities such as dirt and iron powders and an oil layer containing foreign kinds of oil which is generally referred to as a scum are brought to the upper portion of the received emulsion. Of these floating refuse materials, the scum is pumped out into a slush tank 33. The remainder of the soiled emulsion is sent back to the emulsion tank 24 through a filter 35 and pipe 34. The filter 35 eliminates the impurities such as dirt and iron powders still remaining in the emulsion. The above-mentioned circulation line is provided with numerous valves, which are of known type and consequently whose description is omitted.

The emulsion is continuously delivered through the circulation line of the above-mentioned arrangement to an emulsion receiving section 36 or a rolling assembly being supplied with the emulsion, which is enclosed in chain lines in FIG. 6. During circulation, the emulsion gradually decreases in volume and concentration. Accordingly, the emulsion tank 24 is provided with means for replenishing the emulsion. To this end, the emulsion tank 24 is connected to a water tank 38 through a pipe 37 and also to an oil tank 40 through a pipe 39.

There will now be described the mechanism and operation of a system for detecting the concentration of an emulsion running through the rolling assembly and circulation line of the general arrangement.

The emulsion concentration-detecting device 41 of the embodiment of FIG. 6 corresponds to the measuring pipe 1 of the first embodiment of FIG. 1 and is connected to the outlet pipe 25 of the emulsion tank 24 or another pipe branched therefrom (though only the outlet pipe 25 is indicated in FIG. 6). As apparent from the description of FIG. 1, an output signal 13 corresponding to the concentration of an emulsion flowing through the outlet pipe 25 is delivered from the detecting device 41 to a concentration controlling device 42 in the form denoting a value of voltage as shown in a broken line. The concentration controlling device 42 is connected to the later-described ON-OFF valves 43, 44. One ON-OFF valve 43 is provided on a pipe 37 for delivering water from the water tank 38 to the emulsion tank 24, and the other ON-OFF valve 44 is fitted to a pipe 39 for supplying oil from the oil tank 40 to the emulsion take 24. The concentration controlling device 42 compares the emulsion concentration denoted by the output signal 13 with a target value representing a prescribed emulsion concentration, and controls the operation of both ON-OFF valves 43, 44 according to a difference between both concentrations, thereby regulating the amount of water and oil supplied through the pipes 37, 39 so as to regain the proper concentration of an emulsion held in the emulsion tank 24. Said controlling device 42 and two ON-OFF valves 43, 44 collectively constitute an emulsion concentration-controlling unit.

Figure 8:
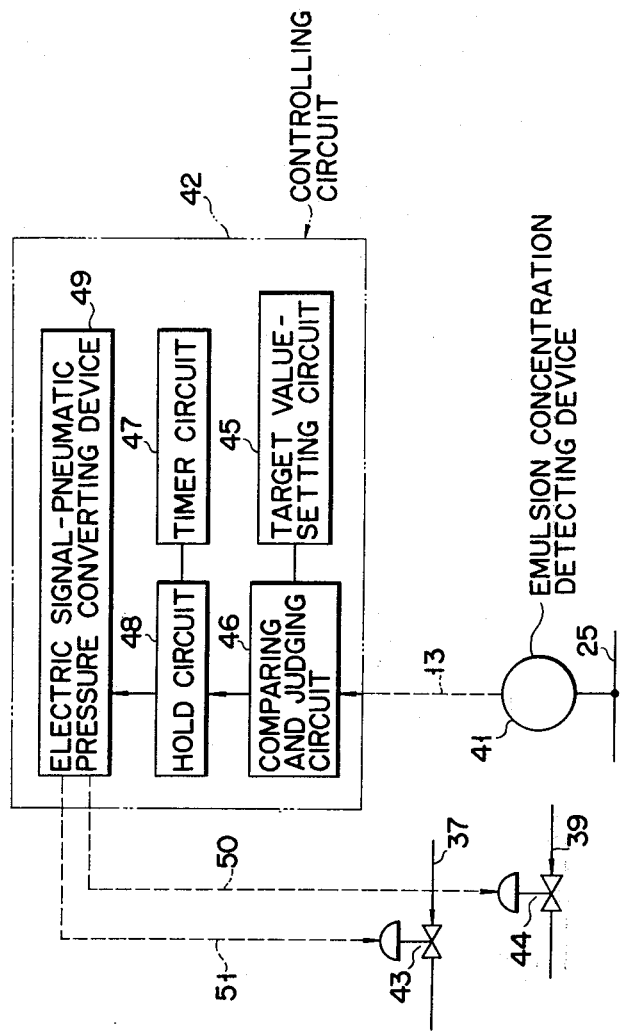
FIG. 8 is a block circuit diagram of a control device used with an emulsion concentration-measuring system according to the embodiments of the invention shown in FIGS. 6 and 7.

FIG. 8 shows the concrete arrangement of the controlling device 42 included in said emulsion concentration-controlling unit. This controlling device 42 consists of a target value-setting circuit 45, comparing and judging circuit 46, timer circuit 47, hold circuit 48 and device 49 for converting an electric signal into pneumatic pressure.

The target value-setting circuit 45 is, for example, a potentiometer. In the target value-setting circuit 45 according to this invention, the proper concentration of an emulsion is taken to be a % and the upper target value of the emulsion concentration is set at $(a + 0.5)\%$ and the lower target value at $(a - 0.5)\%$. Namely, a value of $(a \pm 0.5)\%$ is chosen to be the allowable range of the target emulsion concentration.

The comparing and judging circuit 46 is, for example, a Schmidt trigger circuit. This circuit 46 compares the measured value of the emulsion concentration denoted by the output signal 13 supplied to said circuit 46 and the target value of the emulsion concentration delivered from the target value-setting circuit 45 and, where the measured value falls outside of the target range of $(a \pm 0.5)\%$, sends forth an electric signal to the hold circuit 48. This hold circuit consists of, for example, an electric timer and, where the measured value of the emulsion concentration falls to below the lower target value, delivers an electric signal 50 indicated in a broken line through an electric signal-pneumatic pressure converting device 49 (FIG. 8) to the ON-OFF valve 44 to open it for supply of oil from the oil tank 40 to the emulsion tank 24 for a prescribed length of time, for example, 40 seconds. Where the measured value of the emulsion concentration rises above the upper target value, the hold circuit 48 sends forth an electric signal 51 indicated in a broken line through said converting device 49 to the ON-OFF valve 43 to open it for supply of water from the water tank 38 to the emulsion tank 24 for a prescribed length of time, for example, 80 seconds.

The timer circuit 47 consists of a clock and relay, and causes the control of the emulsion concentration based on its measured value to be carried out at a prescribed time interval. This timer circuit 47 sends forth an electric signal to the hold circuit 48 at an interval of, for example, 20 minutes. Only upon receipt of said signal, the hold circuit 48 delivers an output signal to the ON-OFF valves 43, 44 for control of the emulsion concentration. Since said valves 43, 44 are pneumatically operated, the aforesaid converter 49 is disposed between the hold circuit 48 and said valves 43, 44.

The reason why the target value of the emulsion concentration is chosen to have a prescribed range is that while the measured value of the emulsion concentration falls within said prescribed range, the ON-OFF valves 43, 44 remain inoperative in either way so as to be prevented from being otherwise repeatedly actuated or brought into an oscillating condition, for example, by noise signals sent forth from the detecting device 41. Namely, the prescribed range of the target value acts as a nonsensitive region for suppressing the oscillation of the ON-OFF valves 43, 44.

Experiments with an emulsion controlling unit including the controlling device 42 of the above-mentioned arrangement gave the following results. The automatic control of the emulsion concentration using the controlling unit of this invention was effected, with the amount of the emulsion in the tank 24 set at about 80,000 liters, the outer diameter of a pipe 25 located between the tank 24 and a pump 26 at 457 mm, the flow rate of the emulsion in the measuring pipe at about 10,000 l/mm, the outer diameter of a measuring branch pipe at 100 mm, the feed rate of oil and water respectively at about 300 l/min and the target value of the emulsion concentration at 4%. The experiments showed that during a continuous rolling operation, the measured concentration of the emulsion did not exceed ±15% of the target value, or said excess, converted into concentration, accounted for ±0.6%. In the foregoing experiments, a pipe branched from the pipe 25 was used for measurement. It is obviously possible to use said pipe 25 itself for measurement.

The foregoing experiments proved that the emulsion concentration-controlling system of this invention effectively controlled said concentration without using any manpower in carrying out analysis for measurement of said concentration or replenishing water or oil, thereby elevating the rolling efficiency and providing rolled products of stable quality.

Figure 7:
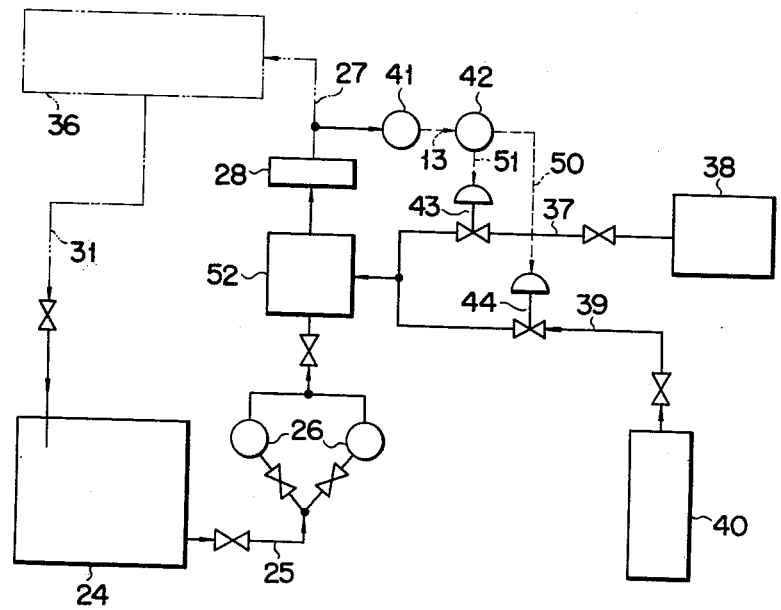
FIG. 7 is a diagram of an emulsion concentration-measuring system according to another embodiment of the invention which is used with the emulsion circulation line of a rolling mill.

FIG. 7 presents a different arrangement from FIG. 6, by which the detecting device 41 and controlling unit are provided for the circulation line of an emulsion. A prominent difference between the arrangements of FIGS. 7 and 6 is that in FIG. 7, a line mixer 52 provided on the outlet pipe 27 of the rolling assembly 36 is connected to the water pipe 37 and oil pipe 39, and that the detecting device 41 is fitted to said outlet pipe 27 instead of the outlet pipe 25 of the emulsion tank 24. The other arrangement of FIG. 7 is the same as that of FIG. 6, and the members included in said other arrangement are denoted by the same referential numbers, description thereof being omitted. The arrangement of FIG. 7 is more advantageous than that of FIG. 6 in that the controlling unit takes less time in controlling the concentration of an emulsion running through the circulation line, namely effects said control with a quicker response to the measured emulsion concentration, and that the makeup amount of oil or water supplied to the line mixer 52 having a smaller volume than the emulsion tanke 24 of FIG. 6 can be reduced to about 100 l/min each time.

Provision of the line mixer 52 on the outlet pipe of the emulsion tank 24 as in FIG. 7 elevates rolling efficiency and saves manpower. However, the arrangement of FIG. 6 can obviously attain the object of this invention.

Figure 9:
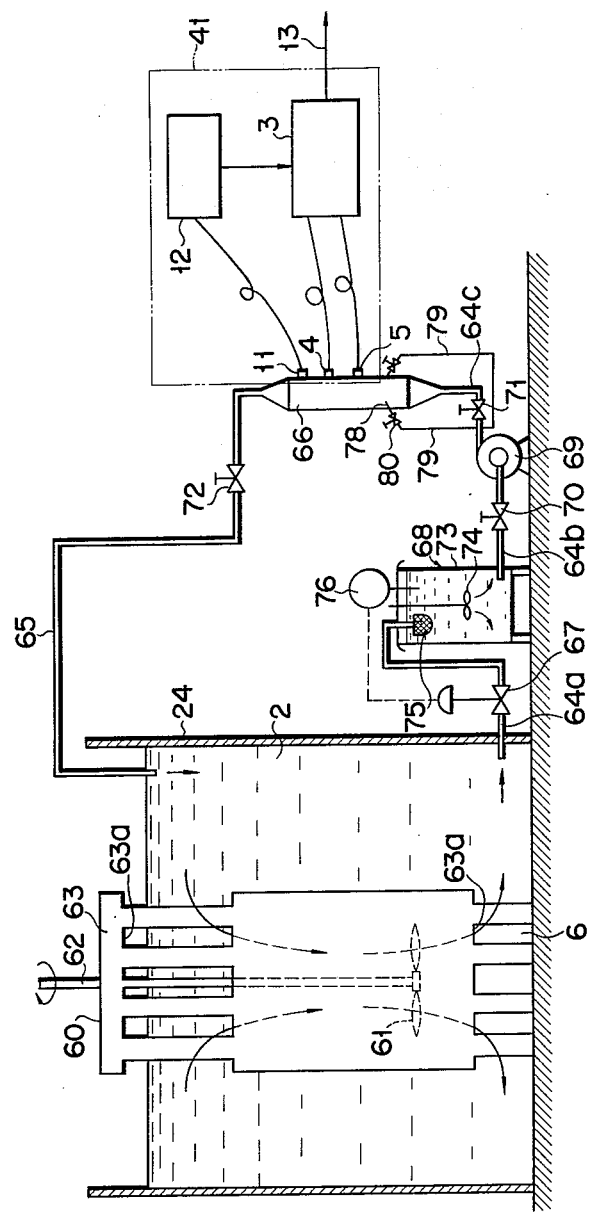
FIG. 9 is a diagram of an arrangement according to still another embodiment of the invention wherein a detecting device is fitted to a pipe for measuring the concentration of an emulsion.

FIG. 9 indicates still another embodiment of the invention, wherein the detecting device 41 is fitted to a separately provided exclusive measuring pipe line, instead of the circulation line of an emulsion.

The emulsion tank 24 has a capacity of about 50 to 150 m³ and contains an agitator 60. This agitator 60 comprises an axial flow type fan 61 used, for example, as a marine propeller or turbine fan, rotary shaft 62 for rotatably supporting said fan 61 and draft tube 63 so disposed as to surround the fan 61 and rotary shaft 62. The upper and lower end portions of the draft tube 63 are bored with numerous slits 63a which extend axially of said tube 63 and are arranged in the peripheral direction thereof. The fan 61 causes an emulsion to be brought into the tube 63 through the upper slits 63a and be discharged therefrom through the lower slits 63a, thereby forcefully mixing the water and oil in the emulsion tank 24 into a homogeneous emulsion.

A pipe line positioned on the right side of the emulsion tank 24 is exclusively used for measurement of the concentration of an emulsion. This pipe line comprises sampling or suction pipes 64a, 64b, 64c, sample feedback pipe 65 and measuring pipe 66 disposed between the suction pipe 64c and feedback pipe 65. The measuring pipe 66 is fitted with a detecting device 41 of the same type as in FIG. 1. The measuring pipe 66 corresponds to the measuring pipe 1 of FIG. 1. Referring to FIG. 9, the detecting device 41 is enclosed in chain lines. The respective members of said detecting device 41, namely, the ultrasonic wave velocity-measuring assembly 3, ultrasonic transmitter 4, ultrasonic receiver 5, temperature detecting section 11 and transducer 12 are all of the same type as those of FIG. 1, description thereof being omitted.

The suction pipe 64a is provided with a control valve 67. A foam-removing device 68 is positioned between the suction pipes 64a, 64b. A pump 69 is disposed between the suction pipes 64b, 64c. These suction pipes 64b, 64c are fitted with valves 70, 71 which are located on the suction and discharge sides of the pump 69 respectively. The suction pipe 64c is connected at one end to the lower end of the measuring pipe 66.

One end of the feedback pipe 66 is connected to the upper end of the measuring pipe 66 and the opposite end is placed in the emulsion through the upper opening of the tank 24. A valve 72 is provided on the feedback pipe 65.

The foam-removing device 68 comprises a small tank 73, an agitation fan 74 placed therein, a filter 75 fitted to the upper end of the suction pipe 64a and a level gauge 76 positioned above said small tank 73. The tank 73 has a capacity of about 50 liters and temporarily holds the emulsion brought from the suction pipe 64a. The filter 75 consists of a screen of steel or cloth of about 60 mesh. The filter 75 removes numerous air bubbles contained in the emulsion before it is carried to the tank 73 through the suction pipe 64a, thereby delivering an emulsion completely free from air bubbles to the tank 73 and reducing the flow rate at which the emulsion is brought into the tank 73. The latter function of the filter 75 enables the emulsion in the tank 73 to have a placid surface, eliminating the possibility of fresh air bubbles being formed.

The agitation fan 74 placed in the tank 73 rotates sufficiently slowly simply to prevent the segregation of the oily component of the emulsion from the water component, thereby maintaining the uniform concentration of the emulsion. The level gauge 76 is electrically connected to the control valve 67 so as to regulate its operation for maintenance of the level of the emulsion in the tank 73.

The detecting device 41 fitted to the measuring pipe 66 transmits ultrasonic waves through the emulsion running through said pipe 66 and detects the concentration of the emulsion from the velocity of ultrasonic waves propagating through the emulsion, as described in connection with FIG. 1.

Figure 10:
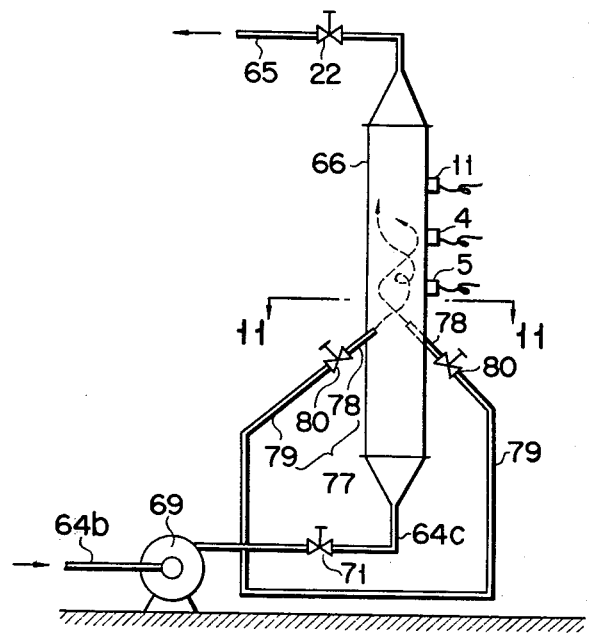
FIG. 10 is a fractional enlarged view of the detecting device of FIG. 9.
Figure 11:
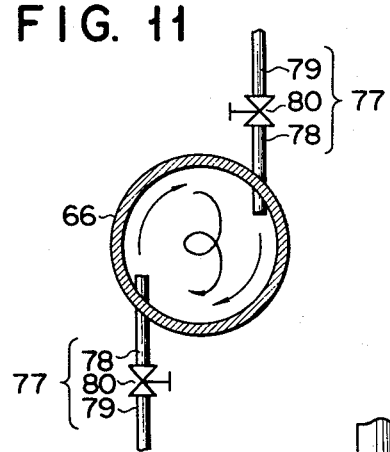
FIG. 11 is an enlarged cross sectional view of a measuring pipe as viewed in the direction of the indicated arrow of FIG. 10 from line 11-11 thereof.

A vortical stream-generating device 77 disposed near the bottom end of the measuring pipe 66 or upstream thereof comprises two nozzles 78 penetrating the peripheral wall of the measuring pipe 66 in a symmetrical relationship with respect to its axis, two branch pipes 79 connecting the nozzles 78 to the suction pipe 64c and two valves 80 provided on said branch pipes 79. As illustrated in FIG. 10, the nozzles 78 penetrate the wall of the measuring pipe 66 in an upwardly inclined state relative to the axial line of said measuring pipe 66 with the open ends directed obliquely upward. The mutually facing open ends of the paired nozzles 78 are disposed, as shown in FIG. 11, near the tangential line on the inner peripheral wall of the measuring pipe 66 so as to eject the emulsion along said inner peripheral wall in the opposite directions of the indicated arrows. The two streams of the emulsion branched from the suction pipe 64c are conducted through the branch pipes 79 and ejected into the measuring pipe 66 at the open ends of the nozzles 78. Said branched streams are mixed with the main stream of the emulsion directly brought into the measuring pipe 66 at the lower end thereof, giving rise to a vortical stream as shown in FIG. 11 to prevent the oily component of the emulsion from tending to be segregated from the water component and attached to the inner wall of the measuring pipe 66 or to scrape off the oily component already settled on said inner wall, thereby attaining the uniform concentration of the emulsion. Provision of the vortical stream-generating device 77 on the upstream side of the measuring pipe 66 immediately ahead of the emulsion concentration detecting point enables the detecting device 41 accurately to measure the propagation velocity of ultrasonic waves or the emulsion concentration.

Figure 14:
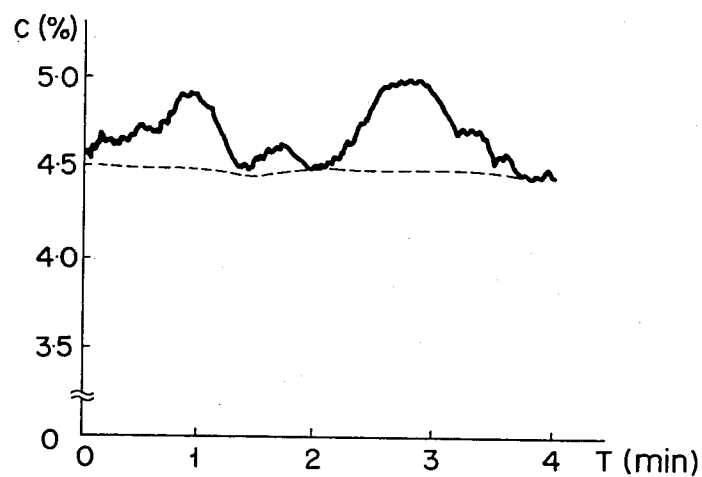
FIG. 14 is a chart comparing the results of measuring the concentration of an emulsion by fitting the detecting device of the invention to the measuring pipe of FIG. 9 with those obtained by the prior art process.

FIG. 14 compares the results of measuring changes with time in the concentration of an emulsion between the case where the above-mentioned vortical stream-generating device 77 was fitted to the measuring pipe 66 and the case where measurement was effected by the prior art process. This experiment was made to find how the emulsion concentration gradually decreased with the time of rolling operation without any replenishment of water and oil. Since the emulsion concentration only changed with time, it was expected that said concentration would fall very slowly. As apparent from FIG. 14, however, the prior art process presented noticeably wide variations in measurement, proving that said process was very unstable, whereas the measuring system of this invention truthfully indicated the very slow changes with time in the emulsion concentration.

Though a pair of nozzles 78 are indicated in FIGS. 10 and 11, the number thereof is not limited to two for the object of this invention.

Figure 13:
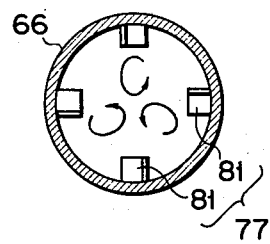
FIG. 13 is a cross sectional view of the measuring pipe of FIG. 12 as viewed in the direction of the indicated arrow of FIG. 12 on line 13-13 thereof.
Figure 12:
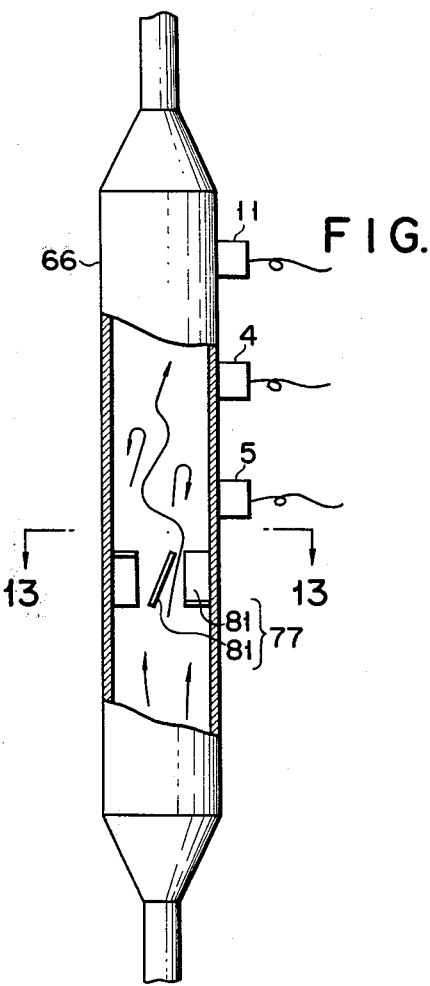
FIG. 12 is an enlarged view of a measuring pipe comprising a modification of a vortical stream-generating device according to still another embodiment of the invention.

FIGS. 12 and 13 show another form of vortical stream-generating device 77. According to this embodiment, the above-mentioned nozzles 78 are replaced by a plurality of inclined baffle plates 81. The four baffle plates 81 shown in FIG. 13 are disposed at right angles to the inner wall of the measuring pipe 66 and inclined at a prescribed angle to the axis of said pipe 66. These baffle plates 81 are located slightly upstream of the point at which the detecting device 41 carries out detection. Accordingly, an emulsion rising from the bottom end of the measuring pipe 66 passes between the inclined baffle plates 81 in a vortical stream to the detection point, preventing the segregated oily component of the emulsion from sticking to the inner wall of the measuring pipe 66 and in consequence attaining the very accurate stable measurement of the emulsion concentration.

What we claim is:

1. A system for measuring and controlling the concentration of a plural component emulsion comprising:
   a measuring means receiving at least a portion of said emulsion and including a circulation line conducting at least a portion of the emulsion through the measuring means; and a detecting device coupled to said circulation line for detecting the concentration of said emulsion and for generating an output signal corresponding to said concentration, thereby determining the concentration of the emulsion conducted through said measuring means; and control means coupled to said detecting device and supplied with an output signal delivered from said detecting device to control the concentration of the emulsion flowing through said measuring means to a desired level;

said detecting device including an ultrasonic transmitter for emitting ultrasonic waves into said emulsion conducted through said measuring means; an ultrasonic receiver for receiving ultrasonic waves emitted into said emulsion from said ultrasonic transmitter and for generating an electrical output signal; a device for generating an electrical signal corresponding to the velocity of the ultrasonic waves propagating through said emulsion, in response to said electrical output signal delivered from said ultrasonic receiver; a device for detecting the temperature of an emulsion conducted through said measuring means and generating an electrical signal corresponding to said detected temperature; and a temperature compensation device for correcting a signal corresponding to the propagation velocity of said ultrasonic waves as a function of a signal corresponding to the temperature of the emulsion by the joint action of said electrical signal generated by said propagation velocity signal-generating device and said electrical signal delivered from said temperature signal-generating device, thereby producing an output signal corresponding to the actual concentration of said emulsion.

2. A system according to claim 1, wherein the ultrasonic transmitter and ultrasonic receiver are coupled to the measuring means with a prescribed spacing therebetween.

3. A system according to claim 1, wherein the detecting device comprises means for supporting the ultrasonic transmitter and ultrasonic receiver in an emulsion flowing through the measuring means with a prescribed spacing therebetween; and a reflecting device for reflecting ultrasonic waves emitted from the ultrasonic transmitter toward the ultrasonic receiver so as to fix the length of the propagating course of ultrasonic waves from the transmitter to the receiver.

4. A system according to claim 3, wherein the supporting means comprises a rectangular frame including at least one pair of side boards, and the ultrasonic transmitter and ultrasonic receiver are fitted to one of said side boards with a prescribed spacing therebetween; and the reflecting device comprises a reflecting plate integrally formed substantially at the center of the other side board.

5. A system according to claim 1, which further comprises an emulsion storing device coupled to the circulation line; an emulsion receiving unit coupled to the circulation line and periodically supplied with an emulsion from the emulsion storing device; and additional supply means for additionally supplying fresh components of the emulsion to the contents of the circulation line.

6. A system according to claim 5, wherein the emulsion receiving unit includes a rolling mill, the emulsion storing device includes an emulsion tank and the emulsion is a mixture of lubricating rolling oil and water.

7. A system according to claim 5, which further comprises a line mixer provided on the circulation line and coupled to the additional supply means for enabling the respective components of an emulsion to be controllably supplied to the circulation line.

8. A system according to claim 5, wherein the additional supply means include feed pipes for delivering the respective components of an emulsion; and the control means comprise valves coupled to said feed pipes and a controlling unit for selectively operating said valves according to an output signal from the detecting device.

9. A system according to claim 8, wherein the valves are mechanically operated valves.

10. A system according to claim 9, wherein the control means comprises a device for setting a predetermined target value for the concentration of the emulsion and generating an electrical signal denoting said target value; a comparing means for comparing an output signal from the target value-setting device and an output signal from the detecting device and generating an electrical signal corresponding to a difference between the values of both compared output signals; an operation-sustaining device coupled to the valves for producing an electrical signal which is a function of the output signal from the comparing means so as to maintain selective operation of the valves for a prescribed length of time; a timing device coupled to the operation-sustaining device for setting the point of time at which the operation-sustaining device generates an output signal; and an electrical signal-converting device coupling the operation-sustaining device to the valves, and for converting an electrical signal received from the operation-sustaining device into a mechanical signal for the selective mechanical operation of the valves.

11. A system according to claim 1, wherein the circulation line includes an emulsion tank; said circulation line is partly used as a separate exclusive measuring pipe line which comprises suction pipes for drawing out an emulsion from the emulsion tank and a feedback pipe for feeding the emulsion back to the emulsion tank; and the measuring means includes a tubular measuring member which is connected to the suction pipes and feedback pipe.

12. A system according to claim 11, wherein the suction pipes include means for removing air bubbles contained in an emulsion running through the exclusive measuring pipe line.

13. A system according to claim 12, wherein the air-bubble removing means includes a filter.

14. A system according to claim 11, wherein the exclusive measuring pipe line includes means for generating a vortical stream in an emulsion conducted through the tubular measuring member.

15. A system according to claim 14, wherein the vortical stream-generating means comprises branch pipes separated from the suction pipe and nozzles fitted to the inner ends of said branch pipes, said nozzles penetrating the wall of the tubular measuring member in a direction upwardly inclined with respect to the axial line of said tubular measuring member.

16. A system according to claim 14, wherein the vortical stream-generating means includes a plurality of baffle plates disposed on the inner wall of the tubular measuring member at right angles thereto, the baffle plates being inclined upwardly at a prescribed angle relative to the axial line of the tubular measuring member.

17. A system according to claim 1, wherein the ultrasonic transmitter and ultrasonic receiver are coupled to the circulation line with a prescribed spacing therebetween.

* * * * *